US006399655B1

(12) United States Patent
de Juan, Jr.

(10) Patent No.: US 6,399,655 B1
(45) Date of Patent: Jun. 4, 2002

(54) METHOD FOR THE PROPHYLACTIC TREATMENT OF CATARACTS

(75) Inventor: Eugene de Juan, Jr., Phoenix, MD (US)

(73) Assignee: Johns Hopkins University, School of Medicine, Baltimore, MD (US)

( * ) Notice: Subject to any disclaimer, the term of this patent is extended or adjusted under 35 U.S.C. 154(b) by 0 days.

(21) Appl. No.: 09/218,956

(22) Filed: Dec. 22, 1998

(51) Int. Cl.$^7$ ............................................... A61K 31/35
(52) U.S. Cl. ..................................... 514/456; 514/912
(58) Field of Search .................................. 514/456, 912

(56) References Cited

U.S. PATENT DOCUMENTS 5,637,703 A 6/1997 Mazurek et al.

FOREIGN PATENT DOCUMENTS

| WO | WO 97/30701 | 8/1997 |
| WO | WO 98/08503 | 3/1998 |
| WO | WO 98/26784 | 6/1998 |
| WO | WO 98/33494 | 8/1998 |
| WO | WO 98/40090 | 9/1998 |

OTHER PUBLICATIONS

Chemical Abstracts 127: 171410 (1997), De Oliveria.*
Calvin et al., "Inhibition of Mouse BSO Cataracts by the Protein Kinase Inhibitor H–7," *Investigative Ophthalmology and Visual Science*, 38, (4 Part 1–2), S1150, (Mar. 15, 1997).
Li et al. "The Redox Active Components $H_2O_2$ and N–Acetyl–L–Cysteine Regulate Expression of c–jun and c–fos in Lens Systems," *Exp. Eye. Res*, 59, 179–190 (Aug., 1994).
Nakai et al., "Aldose Reductase Inhibitors: Flavonoids, Alkaloids, Acetophenones, Benzophenones, and Spirohydantoins of Chroman," *Archives of Biochemistry and Biophysics*, 239 (2) 491–496 (Jun., 1985).
Romero et al., "Pharmacologic Modulation of Acute Ocular Inflammation with Quercetin," *Ophthalmic Res.*, 21 (2), 112–117 (1989) Accepted for publication Jul. 7, 1988.
Shimizu et al., "Inhibition of Lens Aldose Reductase by Flavonoids," *Phytochemistry*, 23 (9) 1885–1888 (Aug., 1984).
de Oliveira et al., *J. Braz. Chem. Soc.* 8(3):211–213 (1997).
Dvornik et al., *Science*, 182: 1146–1148 (1973).
Hutton et al. *Biochemical Pharmacology*, 23: 2991–2998 (1974).
Varma et al., *Documenta Ophtalmol.*, 8: 305–309 (1976).
Agullo et al., "Relationship Between Flavonoid Structure and Inhibition of Phosphatidylinositol 3–Kinase: A Comparision with Tyrosine Kinase and Protein Kinase C Inhibition," *Biochemical Pharmacology*, 53: 1649–1657 (1997).
Akiyama et al., "Genistein, a Specific Inhibitor of Tyrosine–Specific Protein Kinases," *Journal of Biological Chemistry*, 262 (12): 5592–5595 (1987).

Barnes, "Effect of Genistein on In Vitro and In Vivo Models of Cancer," *J. Nutr.* 125: 777S–783S (1995).
Barnes et al., "Biochemical Targets of the Isoflavone Genistein in Tumor Cell Lines," *PSEBM* 208: 103–108 (1995).
Blaise, *Chemical Abstracts*, 81: 13392b (1974).
Burke, Jr. "Protein–Tyrosine Kinase Inhibitors," *Drugs of the Future* 17(2): 119–131 (1992).
Coward et al., "Genistein, Daidzein, and Their β–Blycoside Conjugates: Antitumor Isoflavones in Soybean Foods from American and Asian Diets," *J. Agric. Food Chem.* 41: 1961–1967 (1993).
Cunningham et al. "Synthesis and Biological Evaluation of a Series of Flavones Designed as Inhibitors of Protein Tyrosine Kinases," *Anti–Cancer Drug Design* 7: 365–384 (1992).
Ferris, "Issues in Management of Diabetic Retinopathy," *Hospital Practice*, 79–89 (1993).
Filipeanu et al., "Multiple Effects of Tyrosine Kinase Inhibitors on Vascular Smooth Muscle Contraction," *European Journal of Pharmacology* 281(1): 29–35 (1995) (Abstract).
Fotsis et al., "Genistein, A Dietary Ingested Isoflavonoid Inhibits Cell–Proliferation and In–Vitro Angiogenesis," *Journal of Nutrition* 125(3): 790–797 (1995) (Abstract).
Fotsis et al., "Genistein, a Dietary–Derived Inhibitor of In Vitro Angiogenesis," *PNAS USA* 90: 2690–2694 (1993).
Hagiwara et al., "Differential Effects of Flavonoids as Inhibitors of Tyrosine Protein Kinases and Serine/Threonine Protein Kinases," *Biochemical Pharmacology*, 37(15): 2987–2992 (1988).

(List continued on next page.)

*Primary Examiner*—Zohreh Fay
(74) *Attorney, Agent, or Firm*—Leydig, Voit & Mayer, Ltd.

(57) ABSTRACT

The present invention is directed to a method for the prophylactic treatment of cataract. The method involves the administration of a compound of Formula I

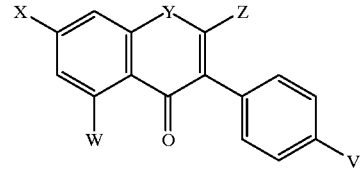

Formula I wherein V, W and X are selected from the group consisting of hydro, hydroxyl, alkoxy, halo, an ester, an ether, a carboxylic acid group, a pharmaceutically acceptable salt of a carboxylic acid group, and —SR, in which R is hydrogen or an alkyl group, Y is selected from the group consisting of oxygen, sulfur, C(OH), and C=O, and Z is selected from the group consisting of hydro and C(O)OR$_1$, wherein R$_1$ is an alkyl, or an analogue or prodrug thereof or a pharmaceutically acceptable salt of any of the foregoing to an animal, such as a mammal, in particular a human, in an amount sufficient to treat cataracts prophylactically. The compound of Formula I is preferably genistein.

31 Claims, No Drawings

OTHER PUBLICATIONS

Hayashi et al., "Activation of Protein Tyrosine Phosphorylation After Retinal Branch Vein Occlusion in Cats," *Investigative Ophthalmology & Visual Science* 38(2): 372–380 (1997).

Hayashi et al., "Increase of Protein Tyrosine Phosphorylation in Rat Retina After Ischemia–Reperfusion Injury," *Investigative Ophthalmology & Visual Science* 37(11): 2146–2156 (1996).

Hayashi et al., "Genistein, a Protein Tyrosine Kinase Inhibitor, Ameliorates Retinal Degeneration After Ischemia–Reperfusion Injury in Rat," *Investigative Ophthalmology & Visual Science* 38(6): 1193–1202 (1997).

Hayashi et al., "Role of Protein Tyrosine Phosphorylation in Rat Corneal Neovascularization," *Graefe's Arch. Clin. Exp. Ophthalmol.* 235: 460–467 (1997).

Herman et al., "Soybean Phytoestrogen Intake and Cancer Risk," *J. Nutr.* 125: 757S–770S (1995).

Kennedy, "The Evidence of Soybean Products as Cancer Preventive Agents," *J. Nutr.* 125: 733S–742S (1995).

Kindy, "Inhibition of Tyrosine Phosphorylation Prevents Delayed Neuronal Death Following Cerebral Ischemia," *Journal of Cerebral Blood Flow and Metabolism* 13: 372–377 (1993).

Koroma et al., "Changes Associated With Tyrosine Phosphorylating During Short–Term Hypoxia in Retinal Microvascular Endothelial Cells In Vitro," *Journal of Cellular Biochemistry* 59: 123–132 (1995).

Koroma et al., "Phosphotyrosine Inhibition and Control of Vascular Endothelial Cell Proliferation by Genistein," *Biochemical Pharmacology* 48(4): 809–818 (1994).

Lamartiniere et al., "Neonatal Genistein Chemoprevents Mammary Cancer," *PSEBM* 208: 120–123 (1995).

Levitzki et al., "Tyrosine Kinase Inhibition: An Approach to Drug Development," *Science* 267: 1782–1790 (1995).

Lu et al., "Effects of Soya Consumption for One Month on Steroid Hormones in Premenopausal Women: Implications for Breast Cancer Risk Reduction," *Cancer Epidemiology, Biomarkers & Prevention* 5: 63–70 (1996).

Moritoki et al., "Possible Involvement of Tyrosine Kinase in the LPS–Promoted Initiation of L–arginine–Induced Relaxation of Rat Aorta Mediated by Induction of $N_o$ Synthase," *Life Sciences* 57(11): PL125–130 (1995) (Abstract).

Ogawara et al., "Inhibition of Tyrosine Protein Kinase Activity by Synthetic Isoflavones and Flavones," *The Journal of Antibiotics*, 42(2): 340–343 (1989).

Ohira et al., "Retinal Ischemia and Cell Proliferation in the Rat: The Role of Soluble Mitogens," *Graefe's Arch Clin. Exp. Ophthalmol.* 228: 195–199 (1990).

Raines et al., "Biology of Atherosclerotic Plaque Formation: Possible Role of Growth Factors in Lesion Development and the Potential Impact of Soy," *Journal of Nutrition* 125(3 Suppl.): 624S–630S (1995) (Abstract).

Steele et al., "Cancer Chemoprevention Agent Development Strategies for Genistein," *J. Nutr.* 125: 713S–716S (1995).

Steusloff et al., "Modulation of Ca2+ Sensitivity in Smooth Muscle by Genistein and Protein Tyrosine Phosphorylation," *Archives of Biochemistry & Biophysics* 320(2): 236–242 (1995) (Abstract).

Varma et al., *Chemical Abstracts*, 86:114978f (1976).

Wilcox et al., "Thrombic Mechanisms in Atherosclerosis: Potential Impact of Soy Proteins," *Journal of Nutrition* 125(3): 631S–638S (1995) (Abstract).

Xiong et al., "Modulation of Ca(2+)–activated K+ Channel Activity by Tyrosine Kinase Inhibitors in Vascular Smooth Muscle Cell," *European Journal of Pharmacology* 290(2): 117–123 (1995) (Abstract).

\* cited by examiner

METHOD FOR THE PROPHYLACTIC TREATMENT OF CATARACTS

TECHNICAL FIELD OF THE INVENTION

The present invention relates to a method for the prophylactic treatment of cataracts.

BACKGROUND OF THE INVENTION

The lens of the eye is a transparent, bi-convex body, which functions as a refractive device to focus light onto the retina. A cataract is an opacity of the lens that adversely affects visual acuity. Cataracts are the leading cause of blindness in the world and incidence of cataract-induced blindness is expected to increase, especially in developing countries. Cataracts can appear at all ages, but are most commonly associated with aging adults—approximately 90% of adults 70 years and older experience symptoms of cataracts. Cataract surgery accounts for the largest single item in Medicare expenditures. In the United States, approximately 1.2 million cataract surgeries are performed every year at a cost of over $3 billion (Taylor, *Journal of the American College of Nutrition*, 12(2): 138–146 (1993)).

The precise cause of cataract formation is unclear. Alteration in cell structure, formation of water pockets, and accumulation of high molecular weight proteins are but a few of the changes in lens architecture associated with cataract formation. Loss of transparency has been linked to formation of opaque fibers in the layers of the lens, as well as loss of transparency of previously clear fibers due to protein damage. Accumulation of extracellular materials and pigment also result in loss of transparency and scattering of light.

Various factors, besides age, have been associated with a predisposition to cataracts. Increased risk of cataract formation has been linked to exposure to ultraviolet light, infection, injury to the eye or the head region, exposure to radiation or toxic substances and prolonged use of corticosteroid drugs. These factors, alone or in concert, predispose one to cataracts by affecting the fibers and the biochemical reactions occurring naturally in the lens. Systemic disease, such as diabetes mellitus, also increases the risk of cataracts. In fact, it has been estimated that diabetics are three to four times more likely to develop cataracts than non-diabetics (Bunce et al., *Annual Review of Nutrition* 10: 223–254 (1990)). While the mechanism of action is unclear, it is believed that osmotic pressure increases with an increase in sugar molecules in the lens and leads to swelling of the lens and subsequently clouded vision.

Symptoms of cataracts include blurred and double vision, color confusion and reduced vision at night and in low light. As vision gradually deteriorates over time, affected individuals lose the ability to accomplish everyday tasks. Decreased vision results in difficulty in reading and watching television. Many have difficulty driving, especially at night. As such, many patients must alter their lifestyles and give up much of their independence. Cataract patients also have an increased risk of injury due to impaired vision.

Unless cataracts seriously interfere with vision and lifestyle, vision correction is accomplished by the prescribing of glasses or contact lenses. Ultimately, however, surgery is required to remove the cataract, once contact lenses and glasses are insufficient to maintain vision. Surgery is comprised of cataract extraction, wherein the affected lens is removed, and, in most cases, replaced with an artificial lens. Cataract surgery can be an outpatient procedure and accomplished with local anesthetic. Still, many complications can arise during and after surgery. Tearing of the capsule of the lens can cause the posterior capsule to rupture, thereby losing the lens to the vitreous cavity. Hemorrhage during surgery can stimulate inflammation and accelerate opacification of the capsule. Epithelial cells can invade the wound into the cornea, iris, and lens capsule, thereby causing uveitis and corneal decompensation. Retinal detachment is also a risk following cataract surgery. A rise in intraocular pressure is common after cataract surgery and causes glaucoma-like symptoms.

Given the prevalence of cataracts, the absence of any mode of prevention of cataracts, and the absence of any mode of treatment beyond surgery, there remains a need for an effective prophylactic treatment of cataracts. Accordingly, it is a principal object of the present invention to provide a method of prophylactically treating cataracts. This and other objects of the present invention will become apparent from the detailed description provided herein.

BRIEF SUMMARY OF THE INVENTION

The present invention is directed to a method for the prophylactic treatment of cataract. The method involves the administration of a compound of the formula:

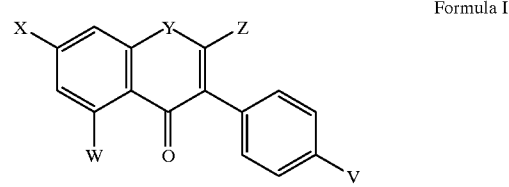

Formula I wherein V, W and X are selected from the group consisting of hydro, hydroxyl, alkoxy, halo, an ester, an ether, a carboxylic acid group, a pharmaceutically acceptable salt of a carboxylic acid group, and —SR, in which R is hydrogen or an alkyl group, Y is selected from the group consisting of oxygen, sulfur, C(OH), and C=O, and Z is selected from the group consisting of hydro and $C(O)OR_1$, wherein $R_1$ is an alkyl. Preferably, the alkoxy is a $C_1$–$C_6$ alkoxy. Preferably, the halo is fluorine, chlorine or bromine. Preferably, the ester is a $C_1$–$C_6$ ester. Preferably, the ether is a $C_1$–$C_6$ ether. Preferred pharmaceutically acceptable salts of the carboxylic acid group include sodium and potassium salts. Preferably, the alkyl groups are $C_1$–$C_6$ alkyl groups. Desirably, the compound of Formula I is genistein.

DETAILED DESCRIPTION OF THE INVENTION

The present invention is predicated on the discovery that compounds of Formula I are effective in the prevention of cataracts. Accordingly, the present invention provides a method for the prophylactic treatment of cataracts. By "prophylactic" is meant the protection, in whole or in part, against cataract formation. The present inventive method is particularly useful in the inhibition of age-related cataracts and diabetic cataracts. However, the present inventive method is also useful in the treatment of cataracts that have been or are being treated with surgery, cataracts that occur after surgical removal of an existing opacified lens, i.e., secondary cataracts, cataracts that occur after retinal detachment and surgery to repair the retinal detachment, cataracts associated with trauma to the eye or head, cataracts associated with tumors, cataracts associated with exposure to radiation, and cataracts associated with toxicity. The present inventive method is also useful in the prophylactic treatment of cataracts resulting from systemic disorders, for example, but not limited to, galactosemia, Farry's disease, Lowe's syndrome, Alport's syndrome and dystrophia myotonica, as well as dermatologic disorders, such as atopy, ichthyosis, Rothmund-Thompson syndrome, Werner's syndrome, incontinentia pigment and Cockayne's syndrome. The present inventive method is also useful in the prevention of cataract formation due to central nervous system disorders, such as neurofibromatosis type II, Zellweger syndrome and Norrie's disease, and local ocular disease, such as glaucoma, uveitis, retinitis pigmentosa, gyrate atrophy, degenerative myopia, ischemia and infection.

The method comprises the administration of a compound of Formula I in an amount sufficient to treat the lens for cataract prophylactically. Accordingly, a compound for use in the method of the present invention is a compound of the following formula:

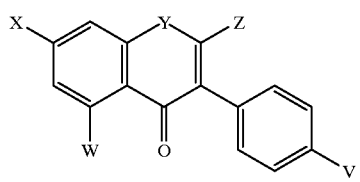

Formula I wherein V, W and X are selected from the group consisting of hydro, hydroxyl, alkoxy, halo, an ester, an ether, a carboxylic acid group, a pharmaceutically acceptable salt of a carboxylic acid group, and —SR, in which R is hydrogen or an alkyl group, and Y is selected from the group consisting of oxygen, sulfur, C(OH), and C=O, and Z is selected from the group consisting of hydro and C(O)OR$_1$, wherein R$_1$ is an alkyl. Preferably, the alkoxy is a C$_1$–C$_6$ alkoxy. Preferably, the halo is fluorine, chlorine or bromine. Preferably, the ester is a C$_1$–C$_6$ ester. Preferably, the ether is a C$_1$–C$_6$ ether. Preferred pharmaceutically acceptable salts of the carboxylic acid group include sodium and potassium salts. Preferably, the alkyl groups are C$_1$–C$_6$ alkyl groups. Preferably, the compound of Formula I is genistein (5,7-dihydroxy-3-(4-hydroxyphenyl)-4H-1-benzopyran-4-one), a pharmaceutically acceptable analogue thereof, a pharmaceutically acceptable prodrug thereof, or a pharmaceutically acceptable salt of any of the foregoing.

The prodrug can be any pharmaceutically acceptable prodrug of genistein, a pharmaceutically acceptable, cataract-inhibiting analogue of genistein, or a pharmaceutically acceptable salt of either of the foregoing. One of ordinary skill in the art will appreciate, however, that the prodrug used must be one that can be converted to an active cataract-inhibiting compound in or around the lens of the eye. A preferred prodrug is a prodrug that increases the lipid solubility of genistein, an analogue of genistein, or a pharmaceutically acceptable salt of either of the foregoing. A preferred prodrug is one in which one or more of V, W and X are independently derivatized with an ester, such as pivalic acid.

Compounds of Formula I are widely available commercially. For example, genistein is available from LC Laboratories (Woburn, Mass.). Those compounds that are not commercially available can be readily prepared using organic synthesis methods known in the art.

Whether or not a particular analogue, prodrug or pharmaceutically acceptable salt of a compound in accordance with the present invention can treat cataract formation prophylactically can be determined, for example, by its effect in the rat model used in Example 1.

The compound for use in the method of the present invention can be bound to a suitable matrix, such as a polymeric matrix, if desired, for use in the present inventive method. Any of a wide range of polymers can be used in the context of the present invention provided that, if the polymer-bound compound is to be used in vivo, the polymer is biologically acceptable (see, e.g., U.S. Pat. Nos. 5,384,333 and 5,164,188).

An advantage of genistein is that it is very safe and efficacious. For example, when genistein was orally administered to Zucker diabetic fatty rats, genistein was found to be nontoxic to the retina at dosages ranging from 75 mg/kg/day to 300 mg/kg/day over a period of six months as measured by electroretinography. In addition, oral administration of genistein was found to have no effect on food intake and body weight for male and female rats. Also, no effect of orally administered genistein was found with respect to the weight of the ovaries and the uterus in female rats.

The compound of Formula I, which is preferably genistein, a pharmaceutically acceptable analogue of genistein, a pharmaceutically acceptable prodrug of genistein, or a pharmaceutically acceptable salt of any of the foregoing, can be administered in accordance with the present inventive method by any suitable route. Suitable routes of administration include systemic, such as orally or by injection, topical, periocular (e.g., subTenon's), subconjunctival, intraocular, subretinal, suprachoroidal, and retrobulbar. The manner in which the compound is administered for the prevention of cataract is dependent, in part, upon the cause of cataract formation.

For example, given that cataract is a risk associated with diabetes mellitus, the compound can be administered as soon as a subject is diagnosed with diabetes. For the prophylactic treatment of cataract that can result from diabetes, the compound is preferably administered systemically, e.g., orally or by injection, although intraocular administration is also acceptable. The compound is preferably administered intraocularly for the prophylactic treatment of secondary cataract formation following cataract surgery.

The prevention of cataract associated with trauma, such as to the eye or head, tumors, exposure to radiation, exposure to toxicity, systemic disorders (for example, but not limited to, galactosemia, Farry's disease, Lowe's syndrome, Alport's syndrome and dystrophia myotonica), dermatologic disorders (such as atopy, ichthyosis, Rothmund-Thompson syndrome, Werner's syndrome, incontinentia pigment and Cockayne's syndrome), central nervous system disorders (such as neurofibromatosis type II, Zellweger syndrome and Norrie's disease) and local ocular disease (e.g., glaucoma, uveitis, retinitis pigmentosa, gyrate atrophy, degenerative myopia, ischemia and infection) involves the administration of the compound by any suitable method, although intraocular administration is often preferred.

The compound of Formula I for use in the present inventive method is preferably administered as soon as possible after it has been determined that an animal, such as a mammal, specifically a human, is at risk for cataract. Treatment will depend, in part, upon the particular compound of Formula I used, the amount of the compound administered, the route of administration, and the cause and extent, if any, of cataract formation realized.

One skilled in the art will appreciate that suitable methods of administering a compound of Formula I, which is useful in the present inventive method, are available. Although more than one route can be used to administer a particular compound of the present inventive method, a particular route can provide a more immediate and more effective reaction than another route. Accordingly, the described routes of administration are merely exemplary and are in no way limiting.

The dose administered to an animal, particularly a human, in accordance with the present invention should be sufficient to effect the desired response in the animal over a reasonable time frame. One skilled in the art will recognize that dosage will depend upon a variety of factors, including the strength of the particular compound of Formula I employed, the age, species, condition or disease state, and body weight of the animal. The size of the dose also will be determined by the route, timing and frequency of administration as well as the existence, nature, and extent of any adverse side effects that might accompany the administration of a particular compound of Formula I and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of from about 1 mg/kg/day to about 100 mg/kg/day, preferably from about 15 mg/kg/day to about 50 mg/kg/day, if administered systemically. Intraocular administration typically will involve the administration of from about 0.1 mg total to about 5 mg total, preferably from about 0.5 mg total to about 1 mg total. A preferred concentration for topical administration is 100 $\mu$M.

Compositions for use in the present inventive method preferably comprise a pharmaceutically acceptable carrier and an amount of a compound of Formula I sufficient to inhibit cataract formation. The carrier can be any of those conventionally used and is limited only by chemico-physical considerations, such as solubility and lack of reactivity with the compound, and by the route of administration. It will be appreciated by one of ordinary skill in the art that, in addition to the following described pharmaceutical compositions, the compound of Formula I can be formulated as polymeric compositions, inclusion complexes, such as cyclodextrin inclusion complexes, liposomes, microspheres, microcapsules and the like (see, e.g., U.S. Pat. Nos. 4,997,652, 5,185,152 and 5,718,922).

The compound of Formula I can be formulated as a pharmaceutically acceptable acid addition salt. Examples of pharmaceutically acceptable acid addition salts for use in the pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulphonic, for example p-toluenesulphonic, acids.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the compound and one which has no detrimental side effects or toxicity under the conditions of use.

The choice of excipient will be determined in part by the compound of Formula I, as well as by the particular method used to administer the composition. Accordingly, there is a wide variety of suitable formulations of the pharmaceutical composition of the present invention. The following formulations are merely exemplary and are in no way limiting.

Injectable formulations are among those that are preferred in accordance with the present inventive method. The requirements for effective pharmaceutically carriers for injectable compositions are well-known to those of ordinary skill in the art (see *Pharmaceutics and Pharmacy Practice*, J.B. Lippincott Co., Philadelphia, Pa., Banker and Chalmers, eds., pages 238–250 (1982), and *ASHP Handbook on Injectable Drugs*, Toissel, 4th ed., pages 622–630 (1986)). It is preferred that such injectable compositions be administered intramuscularly, intravenously or intraperitoneally.

Topical formulations are well-known to those of skill in the art. Such formulations are suitable in the context of the present invention for application to the skin. The use of patches, corneal shields (see, e.g., U.S. Pat. No. 5,185,152), and ophthalmic solutions (see, e.g., U.S. Pat. No. 5,710,182) and ointments, e.g., eye drops, is also within the skill in the art.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inhibitor can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants. Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metals, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-p-aminopropionates, and 2-alkylimidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile -lipophile balance (HLB) of from about 12 to about 17.

The quantity of surfactant in such formulations will typically range from about 5 to about 15% by weight. Suitable surfactants include polyethylene sorbitan fatty acid esters, such as sorbitan monooleate, and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Such compositions can be formulated as intraocular formulations, sustained-release formulations or devices (see, e.g., U.S. Pat. No. 5,378,475). For example, gelantin, chondroitin sulfate, a polyphosphoester, such as bis-2-hydroxyethyl-terephthalate (BHET), or a polylactic-glycolic acid (in various proportions) can be used to formulate sustained-release formulations. Implants (see, e.g., U.S. Pat. Nos. 5,443,505, 4,853,224 and 4,997,652), devices (see, e.g., U.S. Pat. Nos. 5,554,187, 4,863,457, 5,098,443 and 5,725,493), e.g., a mechanical reservoir, an intraocular device or an extraocular device with an intraocular conduit (e.g., 100 μ–1 mm in diameter), or an implant or a device comprised of a polymeric composition as described above, can be used.

The present inventive method can involve the co-administration of other pharmaceutically active compounds useful in the treatment of cataracts. By "co-administration" is meant administration before, concurrently with, e.g., in combination with a compound of Formula I in the same formulation or in separate formulations, or after administration of a compound of Formula I as described above. Preferably, a compound of Formula I can be co-administered with an aldose reductase inhibitor, an antioxidant, or both. Preferably, the aldose reductase inhibitor is selected from the group consisting of carboxylic acids, hydranthoids and related imides. The antioxidant is preferably selected from the group consisting of ascorbic acid, tocopherol, carotenoids, butylated hydroxyanisol, butylated hydroxytoluene, and riboflavin. More preferably, the aldose reductase inhibitor is ponalrestat, epalrestat, sorbinil, imirestat, AND-138, CT-112, zopolrestat, zenarestat, BAL-AR18, AD-5467, M-79175, tolrestat, SPR-210 or oxygen. The carotenoid is preferably zeaxanthin or lutein.

The present invention also provides for co-administration of compounds of Formula I with other pharmaceutically active compounds. For example, corticosteroids, e.g., prednisone, methylprednisolone, dexamethasone, or triamcinalone acetinide, or noncorticosteroid anti-inflammatory compounds, such as ibuprofen or flubiproben, can be co-administered. Similarly, vitamins and minerals, e.g., zinc, and micronutrients can be co-administered. In addition, inhibitors of the protein tyrosine kinase pathway, which include natural protein tyrosine kinase inhibitors like quercetin, lavendustin A, erbstatin and herbimycin A, and synthetic protein tyrosine kinase inhibitors like tyrphostins (e.g., AG490, AG17, AG213 (RG50864), AG18, AG82, AG494, AG825, AG879, AG1112, AG1296, AG 1478, AG126, RG13022, RG14620 and AG555), dihydroxy- and dimethoxybenzylidene malononitrile, analogs of lavendustin A (e.g., AG814 and AG957), quinazolines (e.g., AG1478), 4,5-dianilinophthalimides, and thiazolidinediones, can be co-administered with genistein or an analogue, prodrug or pharmaceutically acceptable salt thereof (see Levitzki et al., *Science* 267: 1782–1788 (1995); and Cunningham et al., *Anti-Cancer Drug Design* 7: 365–384 (1992)). In this regard, potentially useful derivatives of genistein include those set forth in Mazurek et al., U.S. Pat. No. 5,637,703. Selenoindoles (2-thioindoles) and related disulfide selenides, such as those described in Dobrusin et al., U.S. Pat. No. 5,464,961, are useful protein tyrosine kinase inhibitors. Neutralizing proteins to growth factors, such as a monoclonal antibody that is specific for a given growth factor, e.g., VEGF (for an example, see Aiello et al., *PNAS USA* 92: 10457–10461 (1995)), or phosphotyrosine (Dhar et al., *Mol. Pharmacol.* 37: 519–525 (1990)), can be co-administered. Other various compounds that can be co-administered include inhibitors of protein kinase C (see, e.g., U.S. Pat. Nos. 5,719,175 and 5,710,145), cytokine modulators, an endothelial cell-specific inhibitor of proliferation, e.g., thrombospondins, an endothelial cell-specific inhibitory growth factor, e.g., TNFα, an antiproliferative peptide, e.g., SPARC and prolferin-like peptides, a glutamate receptor antagonist, aminoguanidine, an angiotensin-converting enzyme inhibitor, e.g., angiotensin II, calcium channel blockers, ψ-tectorigenin, ST638, somatostatin analogues, e.g., SMS 201–995, monosialoganglioside GM1, ticlopidine, neurotrophic growth factors, methyl-2,5-dihydroxycinnamate, an angiogenesis inhibitor, e.g., recombinant EPO, a sulphonylurea oral hypoglycemic agent, e.g., gliclazide (non-insulin-dependent diabetes), ST638(Asahi et al., *FEBS Letter* 309: 10–14 (1992)), thalidomide, nicardipine hydrochloride, aspirin, piceatannol, staurosporine, adriamycin, epiderstatin, (+)-aeroplysinin-1, phenazocine, halomethyl ketones, antilipidemic agents, e.g., etofibrate, chlorpromazine, spinghosines and retinoic acid and analogues thereof (Burke et al., *Drugs of the Future* 17(2):119–131 (1992); and Tomlinson et al., *Pharmac. Ther.* 54: 151–194 (1992)).

EXAMPLE

The following example further illustrates the present invention but, of course, should not be construed as in any way limiting its scope.

Example 1

This example demonstrates that genistein significantly inhibits cataract formation.

Thirty pair of litter mates of Zucker rats, i.e., thirty male retired breeder Zucker diabetic fatty (ZDF, fa/fa) rats and thirty male retired breeder lean Zucker (fa/+) rats, were obtained (Genetic Models, Inc., Indianapolis, Ind.). The animals were treated in accordance with The Association for Research in Vision and Ophthalmology (ARVO) Statement for the Use of Animals in Ophthalmic and Vision Research. The average blood glucose value was more than 500 mg/dl for the Zucker diabetic fatty rats and 120 mg/dl for the control lean rats as measured by glucose oxidase assay at the time of death (Danis et al. (1993), supra).

Zucker diabetic fatty rats were divided into four groups and fed Purina 5008 rat chow containing varying concentrations of genistein: 0 mg/kg chow, 75 mg/kg chow, 150 mg/kg chow and 300 mg/kg chow. Cataract formation was assessed after six months of treatment. The extent of cataract formation was determined after dilating pupils with phenylephrine (2.5%) and Tropicamide (1%) in rats under general anesthesia resulting from intraperitoneal injections of ketamine (40 mg/kg) and xylazine (4 mg/kg). Disease progression was categorized as total cataract, partial cataract (mainly minimal posterior subcapsular cataract), or no cataract.

TABLE I

|  |  | No Cataract | Partial Cataract | Total Cataract |
|---|---|---|---|---|
| No Genistein | n = 8 |  |  | 8 |
| 75 mg/kg chow | n = 7 |  | 3 | 4 |
| 150 mg/kg chow | n = 8 | 2 | 2 | 4 |
| 300 mg/kg chow | n = 8 |  | 3 | 5 | n = number of rats

Zucker lean rats were also divided into 4 groups and fed Purina 5008 chow containing 0, 75, 150 or 300 mg Genistein/ kg chow. Cataracts were not present in any of the lean control rats after six months of treatment.

The above results illustrate the ability of genistein to inhibit cataract formation associated with diabetes.

All of the references cited herein, including patents, patent applications, literature publications, and the like, are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. A method of prophylactically treating an animal for cataract wherein the animal is at risk of developing cataract, which method comprises administering to said animal a compound of formula I:

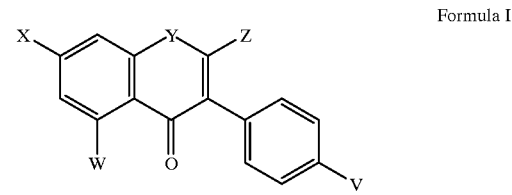

Formula I wherein V, W and X are selected from the group consisting of hydro, alkoxy, hydroxyl, halo, an ester, an ether, a carboxylic acid group, a pharmaceutically acceptable salt of a carboxylic acid group, and —SR, in which R is hydrogen or an alkyl group, and Y is selected from the group consisting of oxygen, sulfur, C(OH), and C=O, and Z is selected from the group consisting of hydro and C(O)OR$_1$, wherein R$_1$ is an alkyl, or a cataract-inhibiting prodrug or pharmaceutically acceptable salt thereof, in an amount sufficient to treat said animal for cataract prophylactically.

2. The method of claim 1, wherein the halo group is selected from the group consisting of fluorine, chlorine and bromine.

3. The method of claim 1, wherein the ester is a $C_1$–$C_6$ ester.

4. The method of claim 1, wherein the ether is a $C_1$–$C_6$ ether.

5. The method of claim 1, wherein said pharmaceutically acceptable salt of a carboxylic acid group is a sodium salt or a potassium salt.

6. The method of claim 1, wherein the alkyl groups are $C_1$–$C_6$ alkyl groups and the alkoxy group is a $C_1$–$C_6$ alkoxy group.

7. The method of claim 1, wherein said compound is genistein.

8. The method of claim 1, wherein genistein is administered systemically.

9. The method of claim 8, wherein genistein is administered in an amount from about 1 mg/kg/day to about 100 mg/kg/day.

10. The method of claim 9, wherein genistein is administered in an amount from about 15 mg/kg/day to about 50 mg/kg/day.

11. The method of claim 8, wherein genistein is administered orally or by injection.

12. The method of claim 1, wherein genistein is administered topically, subconjunctivally, retrobulbarly, periocularly, subretinally, suprachoroidally, or intraocularly.

13. The method of claim 12, wherein genistein is administered by a mechanical reservoir, device or implant.

14. The method of claim 12, wherein genistein is administered intraocularly in an amount from about 0.1 mg total to about 5 mg total.

15. The method of claim 14, wherein genistein is administered intraocularly in an amount from about 0.5 mg total to about 1 mg total.

16. The method of claim 1, wherein said cataract is an age-related cataract or a diabetic cataract.

17. The method of claim 1 wherein said cataract is that which has been treated or is being treated with surgery.

18. The method of claim 1, wherein said cataract is a cataract that occurs after surgical removal of an existing opacified lens.

19. The method of claim 1, wherein said cataract is that which results from retinal detachment and surgery to repair the retinal detachment.

20. The method of claim 1, wherein said cataract is that which results from trauma to the eye or head, a tumor, exposure to radiation or toxicity.

21. The method of claim 1, wherein said cataract is that which results from a systemic disorder, a dermatological disorder, a central nervous system disorder or a local ocular disease.

22. The method of claim 21, wherein said systemic disorder is selected from the group consisting of galactosemia, diabetes mellitus, Farry's disease, Lowe's syndrome, Alport's syndrome and dystrophia myotonica.

23. The method of claim 21, wherein said dermatologic disorder is selected from the group consisting of atopy, ichthyosis, Rothmund-Thompson syndrome, Werner's syndrome, incontinentia pigment and Cockayne's syndrome.

24. The method of claim 21, wherein said central nervous system disorder is selected from the group consisting of neurofibromatosis type II, Zellweger syndrome and Norrie's disease.

25. The method of claim 21, wherein said local ocular disease is selected from the group consisting of glaucoma, uveitis, retinitis pigmentosa, gyrate atrophy, degenerative myopia, ischemia and infection.

26. The method of claim 1, wherein said compound is co-administered with an aldose reductase inhibitor.

27. The method of claim 26, wherein said aldose reductase inhibitor is selected from the group consisting of ponalrestat, epalrestat, sorbinil, imirestat, AND-138, CT-112, zopolrestat, zenarestat, BAL-AR18, AD-5467, M-79175, tolrestat, SPR-210, and oxygen.

28. The method of claim 1, wherein said compound is co-administered with an antioxidant.

29. The method of claim 28, wherein said antioxidant is selected from the group consisting of a carotenoid, ascorbic acid, tocopherol, butylated hydroxytoluene, butylated hydroxyanisol, and riboflavin.

30. The method of claim 29, wherein said carotenoid is selected from the group consisting of zeaxanthin and lutein.

31. The method of claim 28, wherein said compound is further co-administered with an aldose reductase inhibitor.

* * * * *